US00PP09401P

United States Patent [19]

Olesen et al.

[11] Patent Number: Plant 9,401

[45] Date of Patent: Dec. 19, 1995

[54] MINIATURE ROSE PLANT NAMED 'POULGELB'

[75] Inventors: Mogens N. Olesen; Pernille Olesen, both of Fredensborg, Denmark

[73] Assignee: Bear Creek Gardens, Inc., Medford, Oreg.

[21] Appl. No.: 341,652

[22] Filed: Nov. 17, 1994

[51] Int. Cl.[6] ..... A01H 5/00

[52] U.S. Cl. ..... Plt./8.2

[58] Field of Search ..... Plt./8.2

*Primary Examiner*—Howard J. Locker

*Attorney, Agent, or Firm*—Klarquist Sparkman Campbell Leigh & Whinston

[57] ABSTRACT

A miniature rose plant having a strong yellow flower color, ease of propagation from softwood cuttings, long shelf life as a potted blooming rose plant, vigorous, upright, but compact growth, and presentation of flowers in clusters at the top of the plant.

1 Drawing Sheet

The present invention relates to a new and distinct variety of rose plant of the miniature class which was orginated by us by crossing two unnamed seedlings.

The primary objective of this breeding was to produce a new rose variety having strong but compact growth with an excellent display of flowers that would be suitable for growing and forcing in 10 cm pots. Another objective was to develop a seedling with a strong yellow color that could be easily propagated from softwood cuttings. These objectives were substantially achieved, along with other desirable improvements, as evidenced by the following unique combination of characteristics that are outstanding in the new variety and that distinguish it from its parents, as well as from all other varieties of which we are aware:

1. Strong yellow flower color;
2. Ease of propagation from softwood cuttings;
3. Long shelf life as a potted blooming rose plant;
4. Vigorous, upright, but compact growth; and
5. Flowers presented in clusters at the top of the plant.

Asexual reproduction of this new variety by softwood cuttings, as performed at Fredensborg, Denmar, and Somis, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—*Rosa hybrida.*

*Commercial.*—Miniature.

FLOWER

Observations made from specimens grown in a greenhouse environment at Fredensborg, Denmark, and Somis.

Blooming habit: Continuous.

Bud:

*Size.*—7/10 inch long when the petals start to unfurl.

*Form.*—The bud form is pointed ovoid.

*Color.*—When sepals first divide, bud color is Yellow Group 12B. When half blown, the upper sides of the petals are Yellow Group 13C; and the lower sides of the petals are Yellow Group 13C.

*Sepals.*—Color: Green Group 138C. Surface texture: Covered in fine hairs. There are three normally appendaged sepals. There are two unappendaged sepals with hairy edges.

*Receptacle.*—Color: Green Group 137C. Shape: Funnel. Size: Small (¼ inch×¼ inch). Surface: Smooth.

*Peduncle.*—Length: Medium (1¼ inches to 1¾ inches). Surface: Smooth. Color: Medium green. Strength: Stiff, erect.

Bloom:

*Size.*—Small. Average open size is 1½ inches.

*Borne.*—Singly and several together, in clusters of 3 to 5 flowers. If in clusters: Rounded to flat.

*Stems.*—Medium, strong. Average length is about 4½ inches to 5 inches.

*Form.*—When first open: High centered. Permanence: Flattens, outer petals curl back.

*Petalage.*—Number of petals under normal conditions: 35 to 40.

*Color.*—The upper side of the petals is Yellow Group 13C. The reverse side of the petals is Yellow Group 13C. The color of the base of petals is Yellow Group 13C. The major color on the upper side is Yellow Group 13C.

*Variegations.*—None.

*Discoloration.*—The general tonality at the end of the first day: No change. At the end of the third day, no change. On the sixth or seventh day, the yellow color will fade to Yellow Group 14C, especially on the outer petals.

*Fragrance.*—Slight.

Petals:

*Texture.*—Thick.

*Shape.*—Round.

*Form.*—Edges moderately quilled.

*Arrangement.*—Imbricated, with a few petaloids in the center.

*Persistence.*—Drop off cleanly.

*Lastingness.*—On the plant: Very long (12 to 15 days). As a cut flower: Not tested.

Reproductive parts:

*Anthers.*—Size: Medium. Color: Yellow. Arrangement: Regular around styles.

*Filaments.*—Color: Yellow.

*Pollen.*—Color: Lemon yellow.

*Styles.*—Color: Greenish white.

*Stigmas.*—Color: Greenish white.

Form: Bush.

Growth: Vigorous, dwarf, upright, branching, compact. When grown as a 10 cm pot plant, the average height of the plant itself is 6 inches to 7 inches. Outside, in Sourthern California, the plant will reach a height of 18 inches in one season's growth.

Foliage:

*Number of leaflets on normal mid-stem leaves.*— 5.

*Size.*—Small.

*Quantity.*—Normal.

*Color.*—New foliage: Yellow Green Group 146B. Old foliage: Green Group 137A.

Leaflets:

*Shape.*—Pointed oval.

*Texture.*—Upper side: Glossy.

*Edge.*—Serrated.

*Serration.*—Single, small.

*Petiole rachis.*—Color: Green.

*Petiole underside.*—Smooth.

*Stipules.*—Medium, serrated, bearded.

*Disease resistance.*—Resistant to mildew under normal growing conditions at Fredensborg, Denmark, and resistant to mildew and rust under normal growing conditions is Somis, Calif.

Wood:

*New wood.*—Color: Light green. Bark: Smooth.

*Old wood.*—Color: Green. Bark: Smooth.

Prickles:

*Quantity.*—On main canes from base: Few. On laterals from main canes: Few.

*Form.*—Medium, straight.

*Color when young.*—Red.

Small prickles:

*Quantity.*—On main stalks: Few. On laterals: Few.

*Color.*—Green.

We claim:

1. A new and distinct variety of rose plant of the miniature class, substantially as herein shown and described, characterized particularly as to novelty by the unique combination of its strong yellow flower color, its ease of propagation from softwood cuttings, long shelf life as a potted blooming rose plant, vigorous, upright, but compact growth, and presentation of flowers in clusters at the top of the plant.

* * * * *

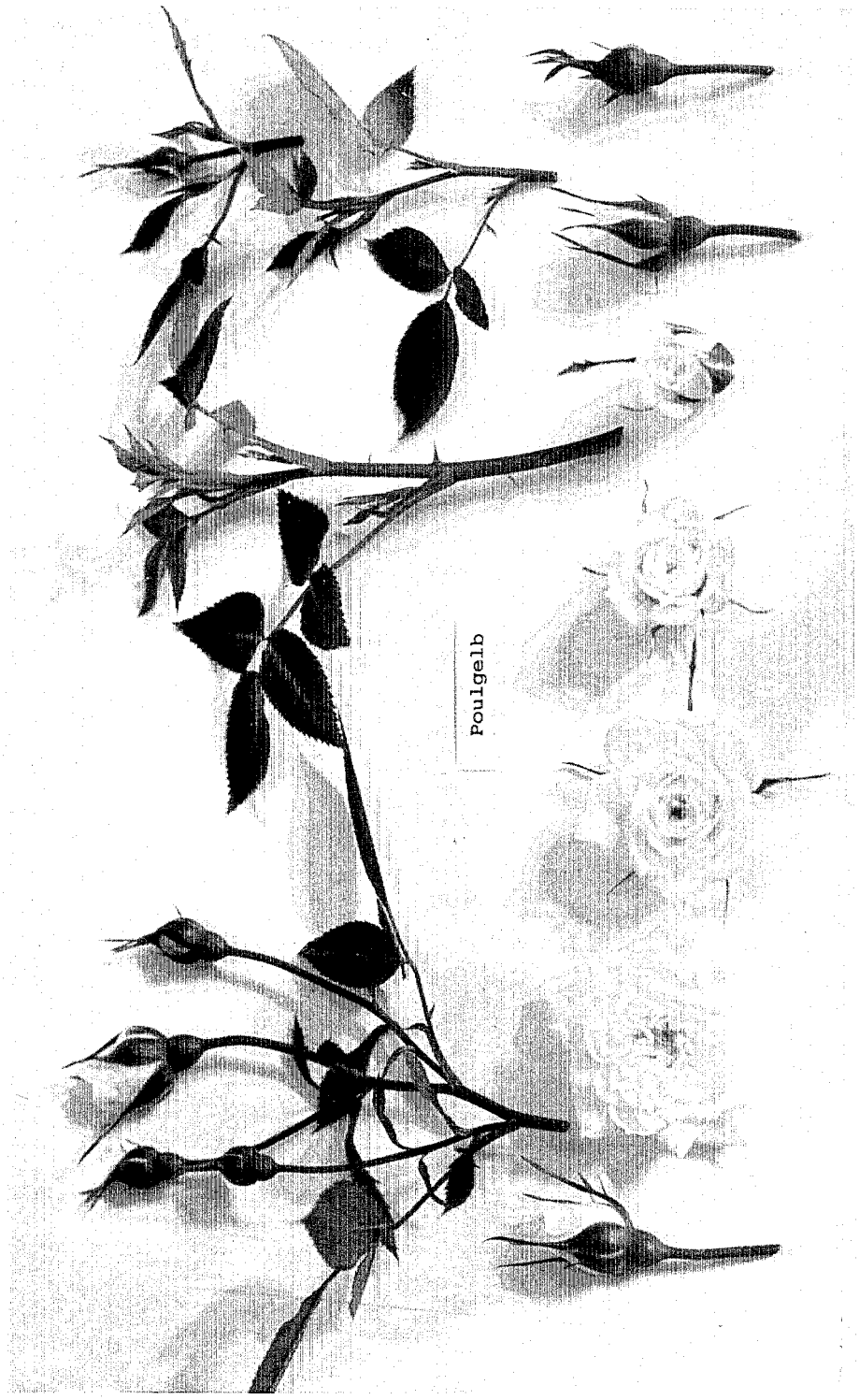
Poulgelb